United States Patent [19]

Nelson et al.

[11] 4,391,151

[45] Jul. 5, 1983

[54] CIRCULAR TWO-STAGE AIR PARTICULATE AND GAS SAMPLER

[75] Inventors: John W. Nelson; Bruno Jensen, both of Tallahassee, Fla.

[73] Assignee: PIXE International Corporation, Tallahassee, Fla.

[21] Appl. No.: 277,833

[22] Filed: Jun. 26, 1981

[51] Int. Cl.³ .................... B01D 50/00; G01N 1/22
[52] U.S. Cl. ........................ 73/863.23; 73/863.25; 55/270
[58] Field of Search ............ 73/863.21, 863.22, 863.23, 73/863.25; 55/270

[56] References Cited

U.S. PATENT DOCUMENTS

| | | | |
|---|---|---|---|
| 3,868,222 | 2/1975 | Barringer | 73/863.25 |
| 3,956,940 | 5/1976 | Guild | 73/863.23 |
| 3,966,439 | 6/1976 | Vennos | 73/863.23 |
| 4,080,832 | 3/1978 | Moody et al. | 73/863.23 |
| 4,152,923 | 5/1979 | Courbon | 55/270 |
| 4,155,247 | 5/1979 | Kaczmarek | 73/863.21 |

FOREIGN PATENT DOCUMENTS

| | | | |
|---|---|---|---|
| 117447 | 12/1957 | U.S.S.R. | 73/863.25 |
| 524999 | 11/1976 | U.S.S.R. | 73/863.25 |

OTHER PUBLICATIONS

"Programmable Control", McClellan, *Popular Electronics*, Apr. 1981, pp. 65-67 & 72-74.

*Primary Examiner*—Howard A. Birmiel

[57] ABSTRACT

A linear filter-type sampling device for pneumatic particulates such as air and/or gases, (sometimes referred to as streaker), wherein a series of at least two complementary samples are taken concurrently with time and size particle information. The device is adapted to deposit on a suitable collector for each sample either a continuous uninterrupted streak of matter or a streak of discrete deposits of matter. A unique feature of the sampling device is achieved through the use of a low pressure vacuum chamber through which a stream of aerosol continuously flows, said chamber having a fixed collector paired with a rotatable orifice at its inlet and operating in series or cascade with a rotatable collector paired with a fixed orifice at its outlet, and wherein each pair cooperates with its respective inlet or outlet to preserve the flow of air through the succeeding sampling stages with no gain or loss to the external air surrounding the sampler.

6 Claims, 23 Drawing Figures

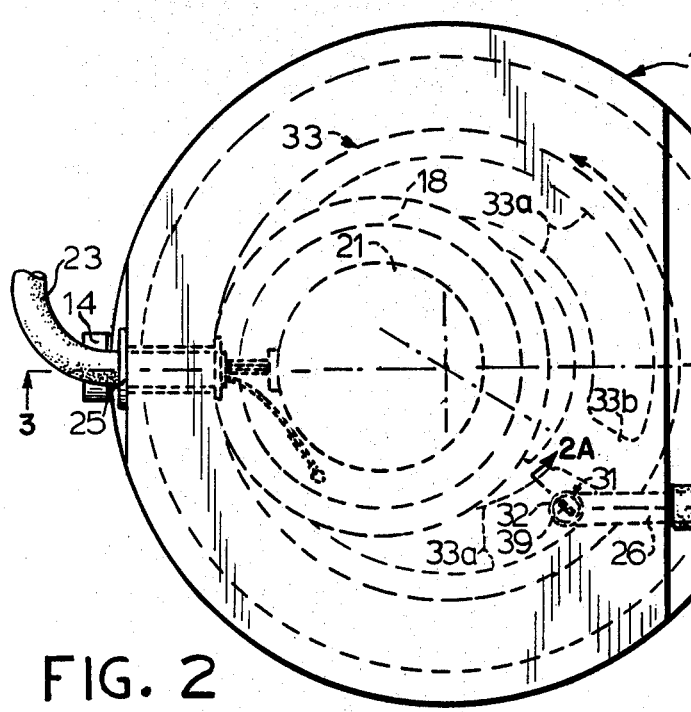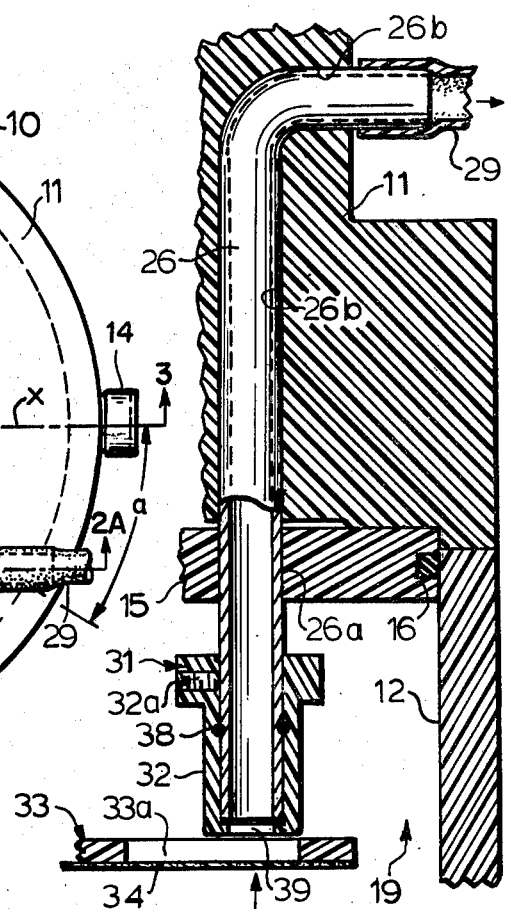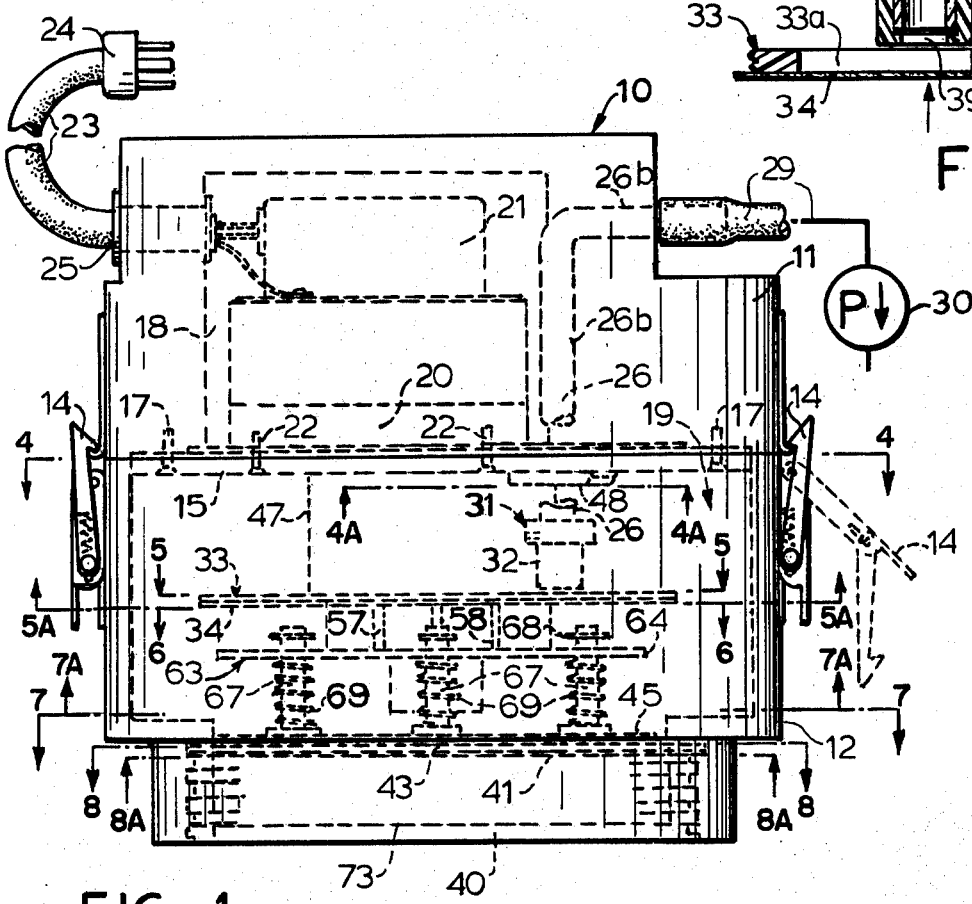

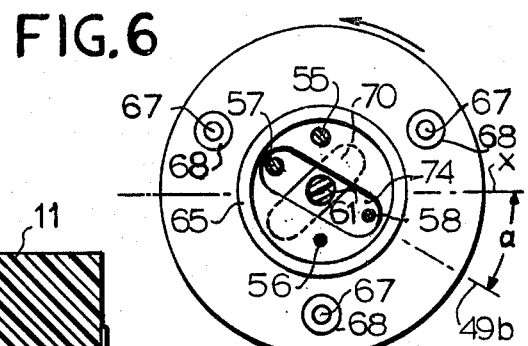
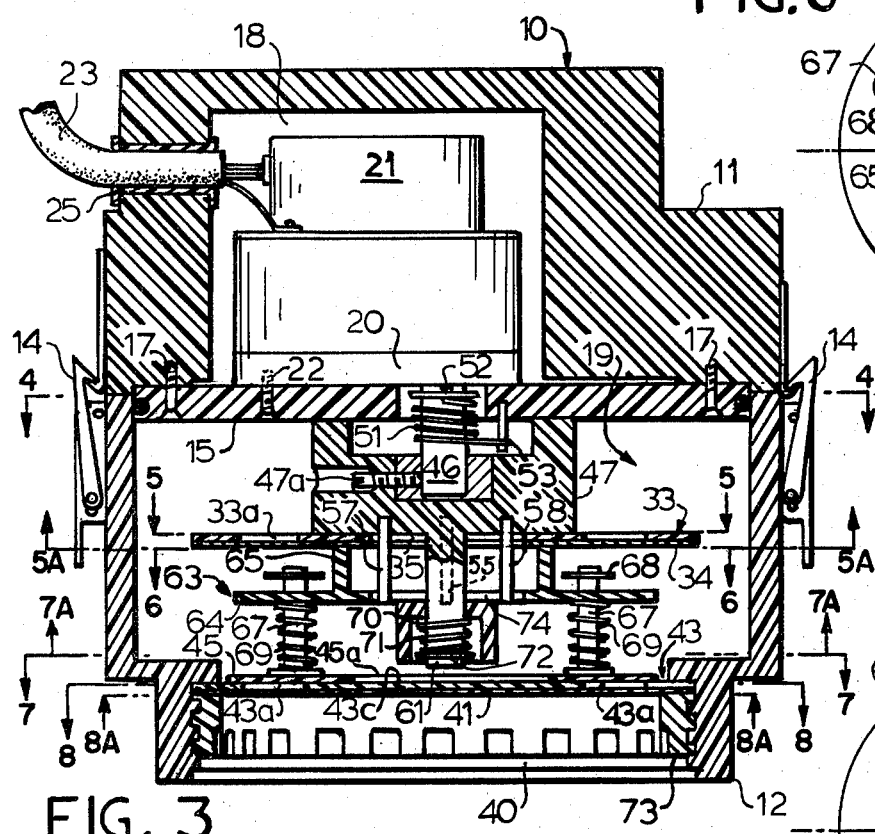
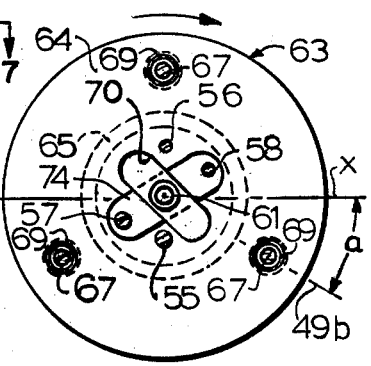
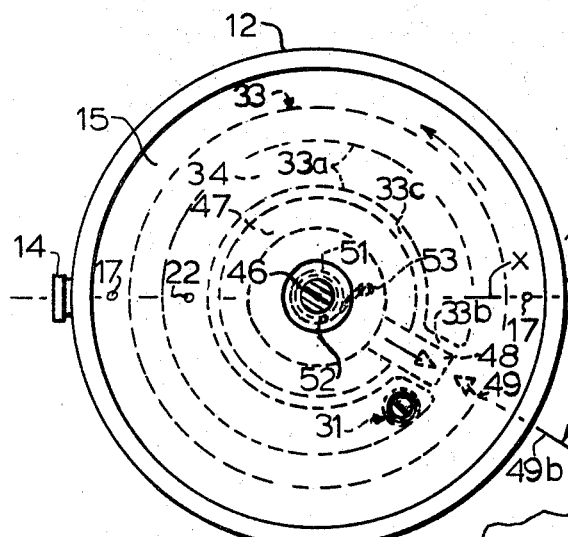
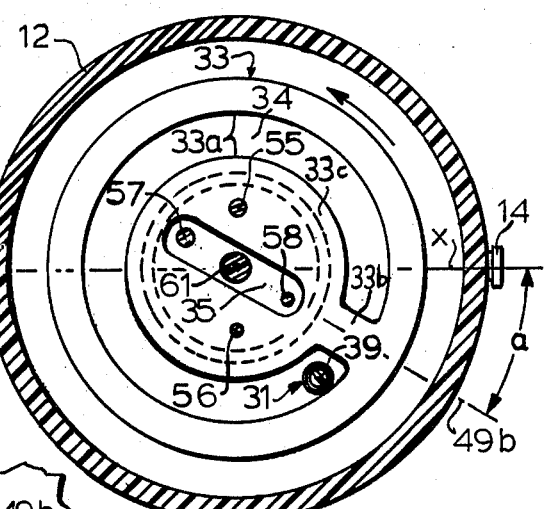
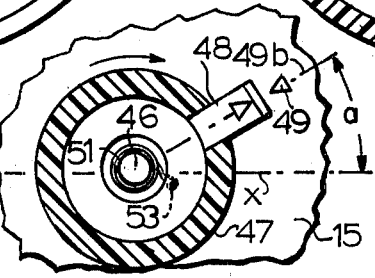

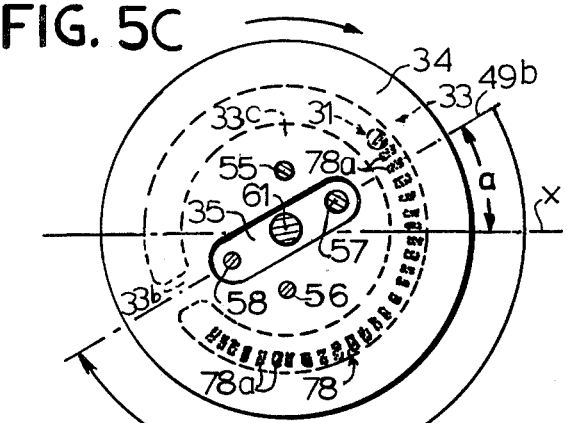
FIG. 5C
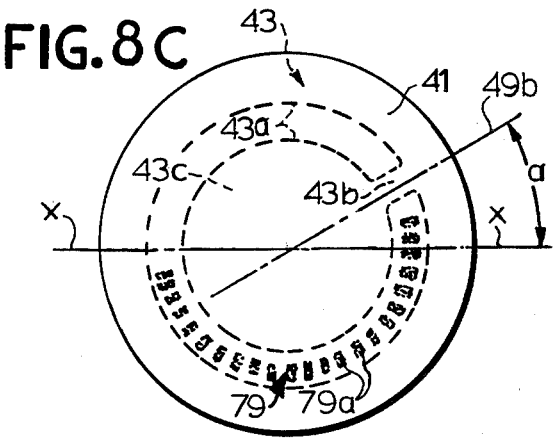
FIG. 8C
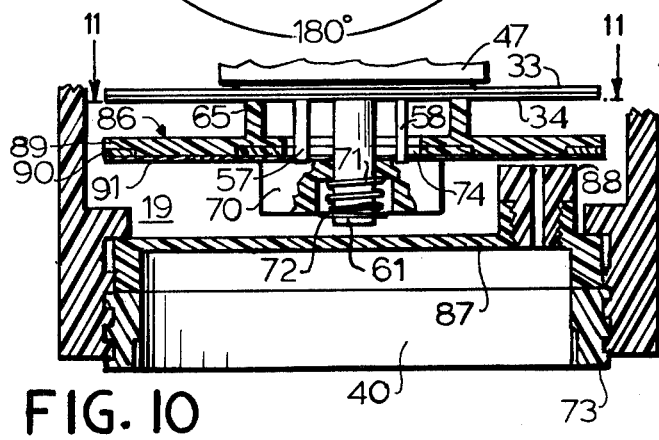
FIG. 10
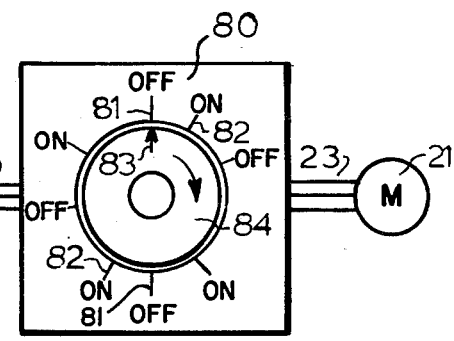
FIG. 13
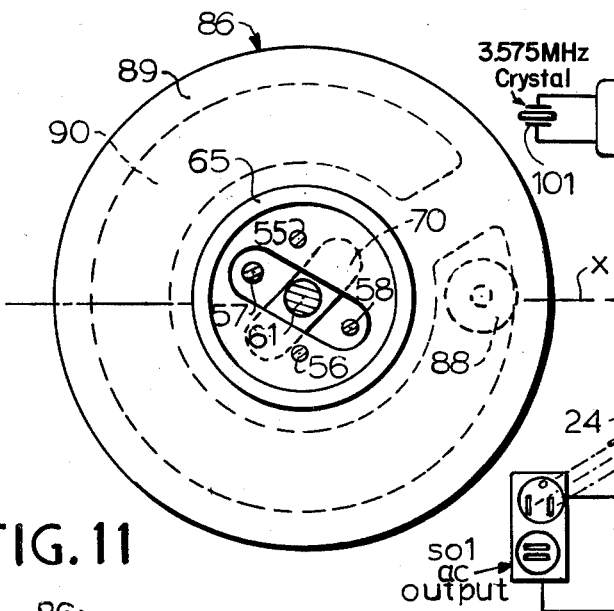
FIG. 11
FIG. 14 PRIOR ART
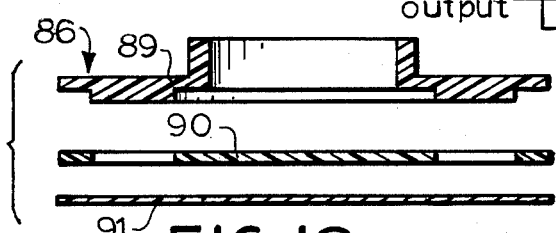
FIG. 12

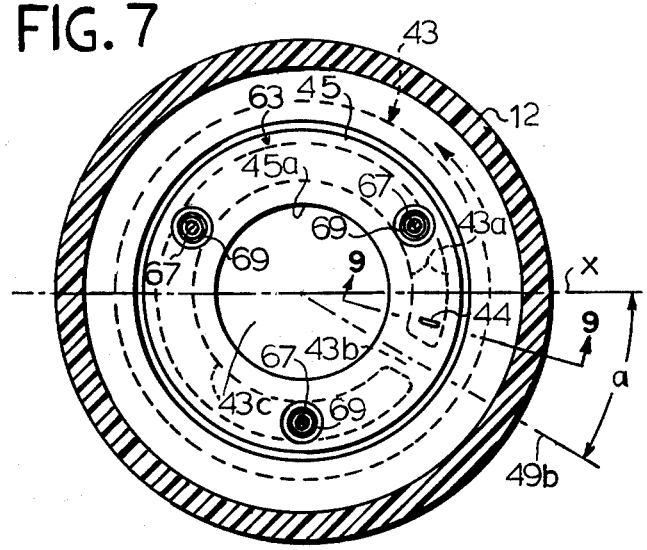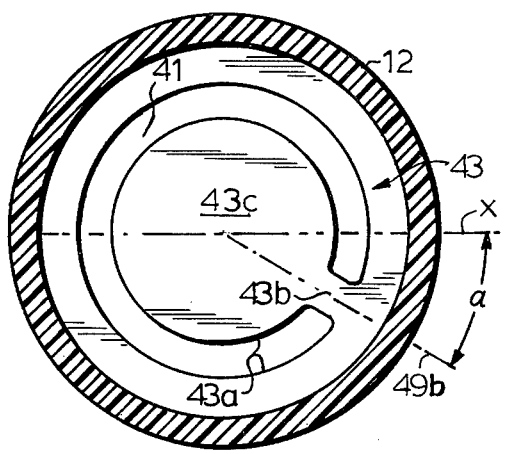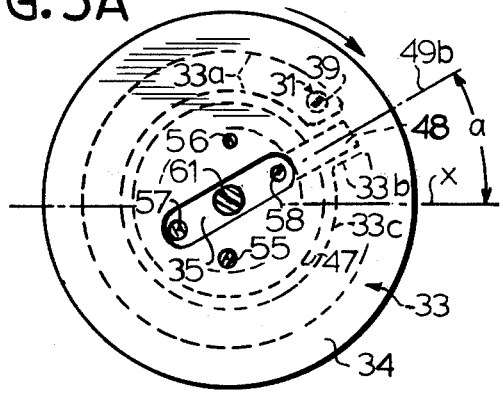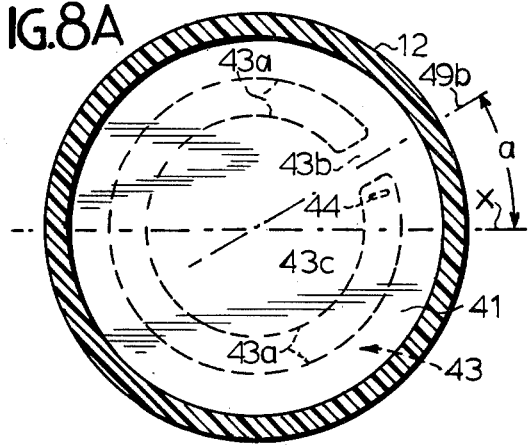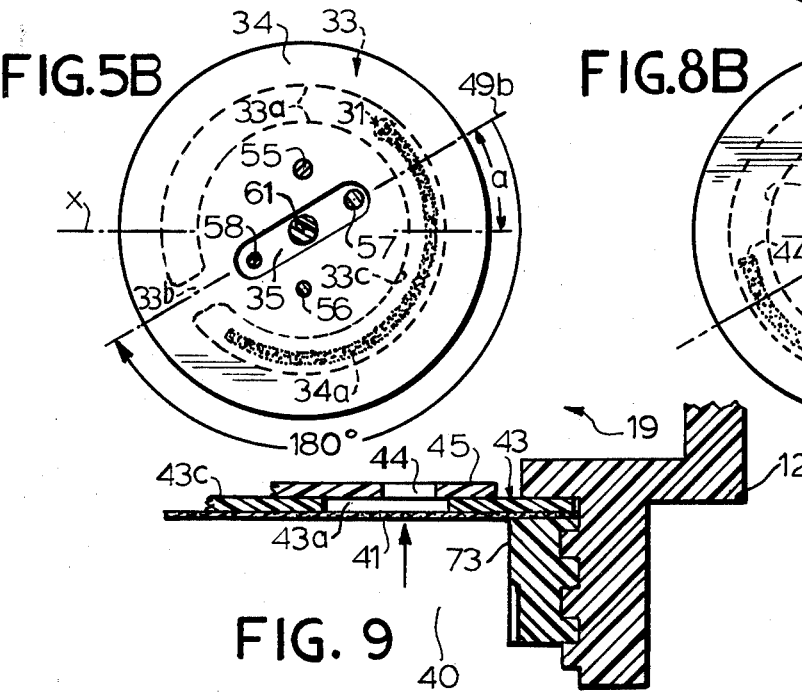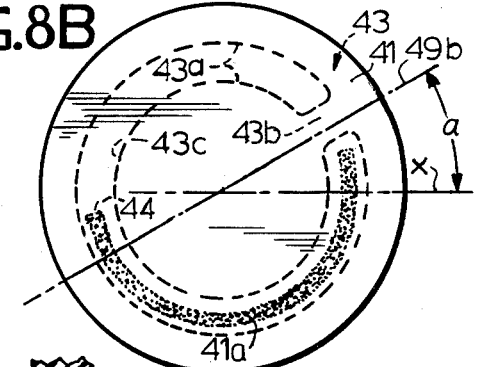

CIRCULAR TWO-STAGE AIR PARTICULATE AND GAS SAMPLER

This invention relates to samplers for pneumatic fluids such as air and/or gases and more particularly to devices of this character for use in conjunction with newly developing analysis methods based upon charged particle beams from accelerators.

Heretofore, numerous methods and devices have been employed for recording particulates of single samples of dirt, smoke and the like in the same atmosphere, as well as for making simultaneous parallel recordings of two or more different atmospheres. U.S. Pat. Nos. 2,310,871; 2,312,295 and 2,675,697 are typical examples of such prior art apparatus. The two first-named patents differ from the present invention in that they operate in parallel rather than in cascade or series and, furthermore, are impaction samplers as opposed to filter samplers. The latter patent concerns a continuously moving filtration type, but likewise is a parallel flow sampler.

So far as applicants are aware, there is no directly applicable prior art which discloses a sampler adapted for use with the newly developing analysis methods based upon charged particle beams from accelerators such as proton induced x-ray emission and proton elastic scattering analyses. Due to the small amounts of matter collected and the form of the sample, other currently used analysis methods (such as wet chemistry, atomic absorption, neutron activation, x-ray excited flourescence) are not as useful. In this regard, the small size of the present sampler, coupled with the tremendous attendant benefits of lower costs and ease of deployment, does not simply represent a miniaturization of the previous art, but rather a novel design to match the characteristics of the new art in the field of quantitative analysis.

It is therefore an object of this invention to provide a pneumatic particulate and/or gas sampler which:

A. embodies a filter or a collector area immediately adjacent a sample that has been exposed to the same ambient air as the sample area;

B. is immediately adaptable to discrete or variable-time continuous sampling, depending upon the type of motor used and its control electronic circuit;

C. functions as a gas sampler when using properly treated filters;

D. optionally, may be operated as a total filter sampler or with dual filter units to provide two size fractions of the aerosol, and E. provides dependable, unattended operation for periods of one week to one month or longer, dpending upon the time resolution needed.

With the foregoing objectives in view, the invention consists of certain novel details of construction and combinations of parts hereinafter more fully described and pointed out in the appended claims. The invention itself, with additional objects and advantages will be best understood from the following description of specific embodiments of operation when read in connection with the accompanying drawings. The mechanical structure is first described followed by a functional description emphasizing novel features. In the accompanying drawings, FIG. 1 is a side elevation of a pneumatic air and/or gas sampler according to the present invention;

FIG. 2 is a top plan view of FIG. 1;

FIG. 2A is an enlarged sectional detail view taken along line 2A—2A in FIG. 2, showing the fixed vacuum orifice structure and the associated rotatable filter assembly;

FIG. 3 is a vertical sectional view taken along line 3—3 in FIG. 2;

FIG. 4 is a sectional plan view taken along line 4—4 in FIGS. 1 and 3;

FIG. 4A is an enlarged sectional detail view taken along line 4A—4A in FIG. 1;

FIG. 5 is a sectional plan view looking downwardly along line 5—5 in FIGS. 1 and 3, showing the rotatable filter support ring 33 and associated filter 34 in sample-starting position, together with the cooperating fixed suction orifice assembly 31;

FIG. 5A is a sectional view looking upwardly along line 5A—5A in FIGS. 1 and 3, this view being substantially opposite-hand to FIG. 5 and shown on sheet 5 of the drawings;

FIG. 5B is a sectional view similar to FIG. 5A, showing a continuous deposit streak 34a on filter 34 after the filter has been rotated approximately 180 degrees from its starting position;

FIG. 5C is a view similar to FIG. 5B, but showing a streak of discrete deposits according to an important modified form of invention, said view being shown on sheet 4 to facilitate comparison with closely related FIG. 8C, described later;

FIG. 6 is a sectional plan view taken along lines 6—6 in FIGS. 1 and 3, showing the moving orifice assembly 63 to the device in starting position;

FIG. 7 is a sectional plan view looking downwardly along line 7—7 in FIGS. 1 and 3, showing the lower part of the orifice assembly 63 and its associated orifice 44 in starting position;

FIG. 7A is a sectional view looking upwardly along line 7A—7A in FIGS. 1 and 3, showing the means for detachably securing the orifice assembly 63 to its driving shaft 61, said view being shown on sheet 2 to facilitate comparison with closely related FIGS. 5 and 6;

FIG. 8 is a sectional plan view looking downwardly along line 8—8 in FIGS. 1 and 3, showing the fixed filter support ring and the attached prefilter 41 in starting position, said view being shown on sheet 3 to facilitate comparison with closely related FIGS. 8A, 8B and 5B and 7;

FIG. 8A is a sectional view looking upwardly along line 8A—8A in FIGS. 1 and 3, said view being substantially opposite-hand to FIG. 8;

FIG. 8B is a sectional view similar to FIG. 8A, showing a continuous uninterrupted deposit streak 41a on the filter 41 after the orifice 44 of assembly 63 has been rotated approximately 180 degrees from its starting position shown in FIG. 7;

FIG. 8C is a view similar to FIG. 8B, but showing a streak of discrete deposits formed thereon simultaneously with those formed on filter 34 and shown in FIG. 5C;

FIG. 9 is an enlarged sectional detail view taken along line 9—9 in FIG. 7, showing the relationship of the fixed prefilter 41, its support ring 43, and the rotatable orifice 44 through which air and/or gases enters the device;

FIG. 10 is a sectional detail view similar to the lower portion of FIG. 3, but showing another modified form of the invention in which a rotatable impact surface structure 86 and a stationary nozzle 88 are employed to record streaks of sample deposits;

FIG. 11 is a sectional plan view taken along line 11—11 in FIG. 10;

FIG. 12 is an exploded sectional view of the components of the impaction surface structure 86 shown assembled in FIGS. 10 and 11;

FIG. 13 is a schematic view, showing another modified form of the invention in which a time control system for motor 21 is used when taking the discrete samples shown in FIGS. 5C and 8C, and FIG. 14 is a schematic view of still another modified form of the invention in which a crystal-controlled, frequency-synthesized dc-to-ac inverter is used to vary the speed of the synchronous motor 21 to permit the use of one sampling device for a variety of time periods.

Referring more particularly to the drawings, the numeral 10 broadly denotes a cylindrical air particulate and gas sampler according to the present invention (FIGS. 1-3).

Sampler 10 comprises upper and lower bodies 11 and 12 respectively, which are detachably joined to one another by any suitable means such as spring-loaded catches 14, 14. A horizontally disposed motor support plate 15 at the junction of bodies 11 and 12 serves as a partition between a low-pressure chamber 19 therebelow and a motor drive assembly recess 18 thereabove, said plate 15 being detachably secured as at 17 to the upper body. In order to provide a tight seal between the perimeter of plate 15 and the inside periphery of lower body 12, an O-ring 16 is mounted in the perimeter of the plate. Plate 15 further serves as a cover for chamber 19 when the bodies 11 and 12 are attached.

A motor-gear train clutch 20 and an associated synchronous motor 21 are housed within the previously-mentioned recess 18, the clutch 20 and its motor being attached to plate 15 by means such as screws 22. As a source of power, an electrical cord 23 having a plug 24 is connected to motor 21, said cord passing through grommet 25 which forms an air-tight seal in the wall of body 11.

The motor support plate 15 further supports a vacuum connection tube (preferably made of metal) which tube is force-fitted through the plate as at 26a and through body 11 as at 26b to thereby provide a suction outlet from the low-pressure chamber 19 to the exterior of the device 10. The upper end of tube 26 is connected to a conduit 28 which, in turn, is connected to a vacuum pump 30 (FIG. 3).

As best shown in FIGS. 2, 2A and 5A, a readily replaceable and vertically adjustable fixed orifice assembly or chamber outlet 31 is mounted on the lower end of tube 26, said assembly consisting of a cup-shaped nozzle 32 adjustably mounted on the tube by means of a set screw 32a whereby the space between the lower end of the nozzle and the filter collector or 34 therebelow may be varied. Proper sealing of nozzle 32 around tube 26 is accomplished with an O-ring 38.

In FIGS. 2, 2A and 5, it will be observed that the bottom wall of nozzle 32 is provided with a rectangular suction orifice 39 which controls the geometric sampling area through filter 34 as the air and/or gases are sucked upwardly from chamber 19, through the filter, through collector or the circular slot 33a in rotary disk 33 and into the orifice.

The circular slot 33a and the orifice assembly 31 are concentrically arranged about the vertical axis common to a drive shaft 46 thereabove and a spindle 61 therebelow, described in detail later. Furthermore, the slot 33a extends about seven-eighths of the distance around the axis of the spindle, leaving the remaining one-eighth distance to provide a connection 33b between the outer portion of the disk 33 and the central portion 33c thereof (FIGS. 4 an 5).

The operation of vacuum pump 30 will cause the pneumatic fluids to be evacuated from chamber 19 and subject it to low pressure which, in turn, will suck the fluids upwardly into the chamber through a relatively large inlet opening 40 in body 12 (FIGS. 1, 3, 7 and 9), through fixed collector or prefilter 41 covering said opening, through a circular slot 43a in fixed prefilter support ring 43, and through a rotary inlet orifice 44 in a disk 45 of assembly 63.

The prefilter or collector 41 retains from the gaseous fluids entering opening 40 those particulates of a predetermined size and larger, while transmitting the smaller size particulates to chamber 19. Similarly, the outlet filter 34 retains the larger particulates of the fluid in chamber 19 and transmits the particulates of a predetermined smaller size to suction pump 30. In this manner, continuous coarse and finer particles are obtained in the cascade filters 41 and 34, respectively.

Like the above-described support ring 33, the fixed prefilter support ring 43 and its associated circular slot 43a and the inlet orifice 44 of assembly 63 are each concentrically arranged about the common vertical axis of shaft 46 and spindle 61. Thus, the slot 43a, the connection 43b and the central portion 43c of ring 43 are identical to parts 33a, 33b and 33c of disk 33, respectively, except that the central portion 43c of ring 43 is imperforate rather than slotted as is the case with central portion 33a (FIGS. 8 and 5).

One useful prefilter 41 consists of the commercially available Nuclepore filter which is adapted to collect those particles greater than 3 millimeters diameter and transmit the smaller particles. The transmitted particles of a smaller diameter in chamber 19 are retained on a similar Nuclepore filter 34 while transmitting still smaller particles as described above. It is to be understood that the characteristics of the filters may be varied to accommodate the conditions of use without departing from the spirit of the invention.

Briefly stated, the axially aligned drive shaft 46 and spindle 61 (FIG. 3) are detachably fixed to one another and rotatable in unison about a common axis to thereby cause the lower support disk 45 and associated orifice 44 (FIG. 9) to rotate relative to fixed inlet filter 41 and, concurrently, to cause the upper disk 33 and associated filter 34 (FIG. 2A) to rotate relative to fixed outlet orifice 39. The relative rotation between inlet orifice 44 and filter 41 causes a circular streak 41a of larger particulates to be deposited upon the filter 41 (FIGS. 8A and 8B) while the relative rotation between outlet orifice 39 and filter 34 causes a circular streak 34a of the smaller particulates to be deposited upon filter 34 (FIGS. 5A and 5B). The basic purpose of the sampler is to code time along a collector or filter of particulates within a low-pressure space and independently of the surrounding atmosphere.

All of the moving parts of the device are enclosed within the sealed low-pressure chamber 19 to preserve the flow of air through the successive stages with no gain or loss to the external atmosphere surrounding the sampler. This was accomplished with air-tight seals at the joints of all moving parts, especially at said inlet 40, outlet 31 and at the junction of parts 11 and 12 of the device.

Moreover, the power required to operate the design over prolonged periods of time has been dramatically decreased as compared with that required by conventional air samplers to the extent that it is now possible to employ as a prime mover the low-powered economical synchronous motor (approximately 4 watts) illustrated schematically in FIG. 14 and described in detail hereinafter.

In FIGS. 1, 4 and 4A, it will be seen that backlash of drive shaft 46 is damped or eliminated by a coil spring 51 which surrounds the shaft, one end of the spring being secured to the shaft as at 52 and the other end to motor support plate 15 as at 53.

It will be noted in FIG. 3 that pointer know 47 is detachably secured to shaft 46 by means of a set screw 47a, said knob being coaxial with spindle 61 adapted to penetrate a centrally disposed slot 35 extending vertically through both the filter 34 and its support disk 33 (FIGS. 3, 5A and 5B). Two eccentrically disposed pins 55 and 56 of different diameters extend downwardly from knob 47, through holes in the central portion 33c of ring 33, and through the filter 34 on the lower face of the ring, said pins serving the purpose of removably keying ring 33 and filter 34 onto knob 47 in a predetermined angular positon relative to spindle 61. Since the pins of different diameters mate with the holes in the ring and filter, the last-named two parts can be installed only in one angular position on the spindle.

Spindle 61 projects downwardly through slot 74 of orifice assembly 63 (FIGS. 3 and 6), said assembly composed of a horizontally disposed disk or ring 64 having integral therewith an upstanding concentric collar 65 adapted to abut the lower face of filter 34 on ring 33 thereabove. Attached to disk 64 is the previously mentioned circular ring 45 containing the rotatable 44 by means of eccentrically disposed posts 67 attached to and rising from ring 45 (FIGS. 7 and 9).

The upper end of each of the posts 67 slidably penetrates a hole in ring 64 and is provided with a retention ring 68 on its projecting upper end portion to prevent separation on the ring 67 from the post. A compression spring 69 is mounted around each post 67 and between rings 64 and 65, said springs serving to normally press ring 64 and its collar 65 upwardly toward rotary filter 34 and its support ring 33, and to press ring 45 downwardly against stationary prefilter support plate 43.

Disk 45 of assembly 63 has a centrally disposed opening 45a therein which normally closes the above-described imperforate central portion 43c of support ring 43 (FIGS. 3, 7 & 8). By closing opening 45a in this manner during normal operation, air and/or gas entering inlet 40 therebelow will be prevented from passing through the opening, but instead will be required to flow only through the restricted moving orifice 44 into chamber 19 thereby maintaining a low pressure in the latter. When, however, the upper and lower bodies 11 and 12 are separate, the opening 45a and associated orifice assembly remains attached to the upper body 11 while the central portion 43c remains with the lower body thereby uncovering opening 45a to permit manual access to handle 70 for the purpose of removing or installing assembly 63 on spindle 61 (FIGS. 3 and 7A). The end portion of spindle 61 has the handle 70 rotatably mounted thereon by means of a retention ring 73, said spindle having a compression spring 71 disposed therearound and between the retention ring and the handle. The spring 71 normally urges ring 64 and collar 65 upwardly against filter 34 to prevent separation of the orifice assembly 63 from the upper body 11 when the latter is separated from the lower body. At this time, the assembly 63 may be detached by manipulating handle 70 into coinciding position with slots 35 and 74, these slots being similar in shape but slightly larger than the handle whereby the the assembly 63, the filter support ring 33 and its filter 34 may be axially removed from the spindle after the bodies 11 and 12 have been separated.

Two pins 57 and 58 of substantially the same length as previously described pins 55 and 56 extend downwardly from knob 47 through slots 35 and 74 (FIGS. 3, 5, 6 and 7A), said pins 57 and 58 serving as rests for handle 70 when in coinciding position with the slots and during removal and installation of assembly 63, support ring 33 and filter 34.

The rotatable knob 47 is provided with a radially extending pointer arm 48 positioned immediately below motor support plate 15 (FIGS. 1, 4 and 4A). When the arm and knob are in sample starting position, the arm is aligned with a scribe mark 49 on plate 15, as well as with an imaginary radial dot-dash line 49b which forms an acute angle "a" with a horizontal imaginary dot-dash axis "x". When the device is in normal sample starting position, the arm 48 is parallel to each of the radial lines 49b in FIGS. 5, 5A, 5B, 5C, 6, 7, 7A, 8, 8B, 8C and 11.

Means are provided for forming continuous complementary deposits of coarse and fine particles from the pneumatic fluids over long periods of time and on the cascade filters or collectors 41 and 34, respectively. In the above-described embodiment, such a deposit is formed on prefilter 41 by causing motor 21 and clutch 20 to continuously rotate the orifice 44 of assembly 63 in a counterclockwise direction from its starting position as shown in FIG. 7 to cause the coarse particles to be deposited upon the lower face of stationary prefilter 41 in the form of a continuous uninterrupted streak 41a (FIG. 8B) while transmitting the relatively smaller particles into chamber 19.

Concurrently with the formation of streak 41a, the filter 34 and its associated support ring 33 are rotated in a counterclockwise direction from starting position (FIGS. 4 & 5) relative to the fixed orifice assembly 31 thereabove (FIG. 2A) to cause the larger particles from chamber 19 to be continuously deposited on the lower face of filter 34 in the form of a continuous uninterrupted streak 34a (FIG. 5B) while transmitting the relatively smaller particles to the vacuum pump 30.

By comparing FIGS. 8B and 5B, it will be observed that the deposit streaks 41a and 34a are chronologically deposited on the filters 41 and 34 in opposite senses of rotation. This result is caused by the use of a rotary orifice 44 operating in association with a fixed prefilter 41 to advance the deopsit clockwise in FIG. 8B, and the use of fixed orifice assembly 31 operating in association with the rotary filter 34 which advances the deposit counterclockwise in FIG. 5B.

When a sampling operation has been completed, the used filters 41 and 34 are replaced with fresh filters, said replacement requiring set screw 47a to be loosened to allow knob 47 to be rotated reversely to starting position and then retightening the set screw. Optionally, the set screw need not be disturbed, but instead, the knob 47 may be rotated reversely against the action of the clutch contained in the clutch component 20.

The modified form of invention shown in FIGS. 5C, 8C and 13 shows two streaks 78 and 79 of separated or discrete samples 78a and 79a, respectively, which are concurrently deposited instead of the continuous uninterrupted streaks 34a and 41a in FIGS. 5A and 8A. This result is accomplished by inserting a conventional timer 80 in the power supply line 23 to externally control motor 21. Timer 80 comprises a circumferentially adjustable "on" and "off" stops 81 and 82 which cooperate with stop-actuating means 83 on continuously rotating timer dial 84. By adjusting the positions of the stops 81 and 82, the length of time the motor remains in-operative to cause filter 34 and orifice 44 to remain stationary during the deposit of samples 78a and 79a may be varied and to also vary the time that the motor operates during which the filter and orifice travel to the next stationary deposit-receiving position. With this simple time control, the motor can be programmed to remain inoperative for eight hours, for example, and then to become operative for one minute while the filter and orifice are advanced to the next deposit-receiving positions, thereby permitting only negligible amounts of deposits in the spaces between the discrete samples.

Another modification of the invention consists in the use of a pre-impaction stage for collecting the coarser particles at the inlet 40 of the device 10a while retaining the previously described filter stage for collecting the relatively fine particles at the outlet of chamber 19 (FIGS. 10–12). This is readily accomplished by the substitution of a rotary impaction surface structure 86 in place of the moving orifice structure 63 of the device 10; and the further substitution of a solid disk 87 containing a stationary impaction nozzle or orifice 88 in place of the previously described filter support ring 43 and its attached prefilter 41.

The structure 86 comprises a support 89 on the lower end of spindle 61, an insert member 90 mounted flush-bottom with support 89 and an impaction layer surface 91 attached to the bottom surfaces of assembled members 89 and 90. The surface collector 91 may consist of a thin layer of material commercially known as MYLAR for collecting the coarse particles ahead of the relatively fine particles as previously described. The nozzles 88 are provided with bores of different sizes and may be used in accordance with the bore size required for a particular sampling operation. This extension has the advantage of using an easily built impaction stage for the coarse particles at the chamber inlet 40 while avoiding such a stage for the finer particles at the chamber outlet 31 which require very fine dimensional control by using a collector such as the previously described filter 34 (FIG. 2A). It will be observed in FIGS. 3, 7 and 9 and at the outlet 40 that the orifice assembly 44, 45 is rotatable and its associated collector 41 is stationary, whereas, in FIGS. 10 and 11 at the same outlet the corresponding orifice 88 is stationary and its associated collector or impaction surface 91 is rotatable in accordance with a modified form of the invention. Nevertheless, the rotatable member at inlet 40 of each form of the invention is disposed completely within the low-pressure chamber 19 and mounted so as to preserve the flow of air into the chamber with no gain or loss to the external atmosphere, as previously described.

FIG. 14 shows another modified form of the invention in which the sampling device 10 is controlled by varying the frequency of the synchronous motor 20 to permit the use of one sampler for a variety of time periods. Small synchronous motors (2 to 6 watts) such as employed with the present sampler are readily susceptible to frequency control and may be operated over a speed range of 8:1 or greater simply by changing the frequency of the alternating current. A detailed disclosure of a commercially available speed control of this type which is peculiarly suited for applicants' purpose appears in *Popular Electronics*, April 1981, on page 65. So far as applicants are aware, such a control has never been used in combination an air sampler previous to this invention. This control is schematically illustrated in FIG. 14 and described below substantially as set forth in the above magazine.

Sometimes it is desirable to vary the speed of a synchronous motor. This article describes a project, the Programmable Speed Control, that provides this capability. It converts +12-volt dc into line-voltage square wave ac whose frequency is crystal-controlled and selectable in 0.1-Hz increments from 10.00 to 100.0 Hz. The project can provide up to 15 watts of output power, and can be modified to provide more. When properly calibrated, it has a rated frequency accuracy six times greater than that of the U.S. ac power grid.

About the Circuit. The heart of the system (FIG. 14) is a phase-locked loop comprising IC1, IC2, IC3, thumbwheel switches Si through S3, and quartz crystal 101. An oscillator in chip IC1 generates a 3.5795-MHz signal whose frequency is controlled by the quartz crystal. Also included in this chip is a programmable-modulo counter. For this application, the counter is programmed so that a 100-Hz square wave appears at its output. This signal is used as a stable reference input for the phase-comparator section of phase-locked loop IC2.

Applied to the other output of the phase comparator is a square wave derived from the output of the voltage-controlled-oscillator section (vco) section of IC2. The output of the vco is a square wave whose frequency can vary from 10 to 100 kHz. In the example shown, it is nominally 60 kHz. This signal is applied to the programmable-modulo counter IC3, which divides its frequency by a factor determined by the settings of thumbwheel switches S1, S2, and S3. These switches generate twelve bits which are applied to the programming output of IC3 and whose decimal equivalent is read off the faces of the switches.

In FIG. 14 the switches are shown set to read 60.0, but the decimal equivalent of the number actually applied to the counter is 600. Accordingly, the vco output frequency is divided by 600, and a 100-Hz square wave appears at the output of IC3. The phase comparator accepts the two square-wave inputs. If they are not in phase the comparator sends a "dc error voltage" to the control input of the vco. In response, the vco shifts its frequency of oscillation until the square wave generated by IC3 is in phase with the quartz-derived reference. (Frequency can be considered the rate of change of the phase). At this point, the output of the vco comparator is phase-locked to the reference.

Switches S1, S2, and S3, together with IC1, IC2, and IC3 form a frequency synthesizer that generates an extremely stable square wave. Its frequency will be between 10 and 100 kHz, the exact value determined by the settings of the thumbwheel switches. Counters IC4 and IC5 divide the vco output frequency by a factor of 1000. For the example shown, the output of IC5 is 60.0 Hz. Counter IC5 functions such that the duty cycle of its square-wave output is 50 percent.

This signal is inverted by buffer IC6F, whose output is simultaneously applied to driver Q1 and to inverting buffer IC6A. The output of the second inverting buffer is applied to driver Q2. When Q1 is conducting, it provides base drive to power transistor Q4, but driver Q2 and, hence, power transistor Q3 are cut off. Similarly, when the output of IC6A causes Q2 and Q3 to conduct, Q1 and Q4 are cut off. The emitters of the power transistors are grounded, and their collectors are connected to the ends of the secondary winding of transformer T1. The center tap of the secondary is connected to +12 volts as at 102.

Power transistors Q3 and Q4 cause current pulses of opposite polarity to flow through the secondary of T1. Actually, the nominal secondary is used as a primary winding in this application and vice versa. Line voltage, square-wave ac appears across the primary of T1 and is routed to power socket SO1. There it is available to the synchronous ac motor 21 through plug 24 and cable 24 whereby the speed of the motor is controlled. Thus its is seen that a crystal-controlled, frequency-synthesized dc-to-ac inverter is provided in combination with the above-described circular two-stage air particulate and gas sampler.

We claim:

1. In a sampling device for the particulate matter of air and gaseous fluids comprising:

(a) a chamber having an inlet and an outlet;

(b) a vacuum pump for sucking said fluid through said inlet into said chamber and through said outlet;

(c) means including an orifice and an associated collector at said inlet for retaining particulates from said fluid of a predetermined size and larger, and for transmitting the particulates thereof of a smaller size into said chamber;

(d) means including a second orifice and an associated collector at said outlet for retaining from the particulates of said chamber those particulates of a predetermined size and larger, and for transmitting the particulates thereof of relatively smaller size, and (e) means for effecting relative rotational movement between the orifice and collector of said first-named means to chronologically form an arcuate deposit on the first collector and, concurrently, for effecting relative movement between the orifice and collector of said second-named means to chronologically form an arcuate deposit on the second collector, (f) one of the orifices of said first and second-named means being fixed and the other movable, and the collector associated with said fixed orifice being movable and the collector associated with said movable orifice being fixed, whereby the arcuate deposits on the respective collectors will read chronologically in opposite directions.

2. A sampling device for the particulate matter of air and gaseous fluids comprising:

(a) a chamber (19) having an inlet (40) and an outlet (31);

(b) a vacuum pump (30) for sucking said fluid through said inlet into said chamber and through said outlet;

(c) a collector member (41) with an associated orifice member (44, 45) at said inlet and adapted to retain from said fluid the coarser particulates of a predetermined size and larger, and to transmit therefrom the finer particulates into said chamber, one of said members being disposed within said chamber and rotatable relative to the other member;

(d) a second collector member (34) with an associated second orifice member (32, 39) disposed within said chamber and adapted to retain from said finer particulates transmitted to said chamber those particulates of a predetermined size and larger, and to transmit therefrom the remaining finer particulates to said outlet, said second collector member (34) being rotatable relative to said second orifice member (32, 39) and about an axis (46) common to the axis of rotation of said first rotatable member (44, 45), and (e) means (20, 63) for effecting rotary movement of said first rotatable member to chronologically form a circular arcuate deposit **(41*a*) of said coarser particulates on said first collector member and, concurrently, for effecting rotary movement of said second collector member (34) to chronologically form a circular arcuate deposit (34*a*)** of said remaining finer particulates retained by said second collector member.

3. The sampling device defined in claim 2 and further comprising time control means (80) for alternately arresting and resuming for predetermined time periods the rotary movement of said first rotatable member, on one hand, and the rotary movement of said second collector (34), on the other hand, to thereby permit accumulation of discrete arcuate deposits **(79*a*, 78*a*)** on the respective collectors.

4. The sampling device defined in claim 2 wherein said means for effecting rotary movement includes a synchronous ac motor (20), and further comprising a frequency synthesizer (IC1, IC2, IC3) provided with a range of frequencies for said ac motor, and means (S1, S2, S3) for selecting frequencies from said range to control the speed of said motor.

5. The sampling device defined in claim 2 wherein said rotatable member at said inlet (40) comprises an imperforate solid base having an impaction surface (91) thereon for collecting said coarser particulates of a predetermined size and larger from the associated orifice (88) while permitting the particulates of relatively smaller size to be transmitted into said chamber and wherein said collector at the outlet comprises a filter (34).

6. The sampling device defined in claim 5 wherein said means for effecting rotary movement of said first rotatable member and of said second collector (34) includes a synchronous ac motor (20), and further comprising a frequency synthesizer (IC1, IC2, IC3) provided with a range of frequencies for said ac motor, and means (S1, S2, S3) for selecting frequencies from said range to control the speed of said motor.

* * * * *